United States Patent [19]

Reckel et al.

[11] Patent Number: 4,595,654
[45] Date of Patent: Jun. 17, 1986

[54] METHOD FOR DETECTING IMMUNE COMPLEXES IN SERUM

[75] Inventors: Rudolph P. Reckel, Bridgewater; Joanne L. Harris, Annandale; Ralph Wellerson, Jr., Basking Ridge; Sally M. Shaw, Somerville; Paul M. Kaplan, Sergeantsville, all of N.J.

[73] Assignee: Immunomedics Inc., Newark, N.J.

[21] Appl. No.: 549,105

[22] Filed: Nov. 7, 1983

[51] Int. Cl.$^4$ .................. G01N 53/00; G01N 33/564; C12N 5/00; C07K 15/04
[52] U.S. Cl. ........................................ 435/7; 530/380; 530/387; 435/68; 435/172.2; 435/240; 435/948; 435/810; 436/506; 436/507; 436/518; 436/531; 436/548; 436/804; 436/808; 436/809; 436/811; 436/815; 436/821; 436/823; 935/104; 935/110
[58] Field of Search .................. 260/112 R; 435/4, 7, 435/68, 70, 172.2, 240, 968; 935/100, 104, 106, 108, 110; 436/506, 507, 509, 518, 536-542, 548, 804, 808-810, 811, 815, 821, 823

[56] References Cited

U.S. PATENT DOCUMENTS

| | | | |
|---|---|---|---|
| 4,062,935 | 12/1977 | Masson et al. | 424/12 |
| 4,138,213 | 2/1979 | Masson et al. | 23/230 B |
| 4,141,965 | 2/1979 | Suthill et al. | 424/12 |
| 4,143,124 | 3/1979 | Masson et al. | 424/12 |
| 4,210,622 | 7/1980 | Suthill et al. | 422/61 |

OTHER PUBLICATIONS

Gabriel, A. et al., J. Clinical Investigation, vol. 59(5), pp. 990-1001 (1977), Abstract/CA, copy ordered.

Golan, M. D. et al., J. Immunology, vol. 129(2), pp. 445-447 (1982), Abstract/CA, copy ordered.

Heinz, H. P. et al., Intercell. Commun. Leucocyte Funct., Parker, J. W. et al. Ed., Wiley, Chichester, U.K. (1983), Abstract CA, copy ordered.

Heinz, H. P. et al., J. Immunology, vol. 132(2), pp. 804-808 (1984), not prior art, Abstract Sent/CA, copy ordered.

Heinz, H. P. et al., J. Immunology, vol. 133(1), pp. 400-404 (1984), not prior art, Abstract sent, copy ordered.

Zubler, R. H. et al., The $^{125}$I-Clq Binding Test for the Detection of Soluble Immune Complexes, in Vitro Methods in Cell-Mediated and Tumor Immunity, by Bloom & David, pp. 565-572, 1976 Acad. Press.

Lachmann, P. J., Studies with Monoclonal Antibodies to Complement Components, Immunology Today, 144, Aug. 1981.

Hautanen, A. et al., C3c-Binding ELISA for the Detection of Immunoconglutinins and Immunoglobulin Aggregates, Methods in Enzymology, vol. 74:39-588-591 (1981).

Pribor, H. C. et al., Circulating Immune Complexes, Clinical Forum, pp. 23-25, May 1979.

Hay, F. C. et al., Routine Assay for the Detection of Immune Complexes of Known Immunoglobulin Class Using Solid Phase Clq, Clin. Exp. Immunol., 24, 396-400 (1976).

Nydegger, U. E. et al., Circulating Immune Complexes in the Serum in Systemic Lupus Erythematosus and in Carriers of Hepatitis B Antigen, J. Clin. Invest., 54:297-309, Aug. 1974.

Rossen, R. D. et al., Detection of Immune Complex--Like Materials in Cancer Patient's Sera: A Comparative Study of Results Obtaining With a Clq Deviation and Clq Binding Tests, J. Lab. Clin. Med., 191-204, Feb. 1978.

Rosen, R. D. et al., Blockade of the Humoral Immune Response: Immune Complexes In Cancer, Chapter 8, Cancer Immunology: vol. 7, Harold Waters, Garland Publication, 1980.

(List continued on next page.)

Primary Examiner—Thomas G. Wiseman
Assistant Examiner—M. Moskowitz

[57] ABSTRACT

Method and test kit for detecting Clq-containing complexes in human serum containing native serum Cl. The method uses a monoclonal antibody which selectively reacts with human Clq in the presence of native human serum Cl. Preparation of hybridomas generating such antibodies is also disclosed. The method is applicable to detection of autoimmune diseases and AIDS.

19 Claims, 1 Drawing Figure

OTHER PUBLICATIONS

Theofilopoulos, A. N., The Raji, Conglutinin, and Anti--C3 Assays for the Detection of Complement-Fixing Immune Complexes, Methods in Enzymology, vol. 74:511–531, 1981.

Siersted, H. C. et al., Quantitation of Circulating Immune Complexes by Combined PEG Precipitation and Immunoglobulin Specific Radioimmunoassay, Methods in Enzymology, vol. 74:538–543, 1981.

Glikmann, G. et al., Detection and Quantitation of Circulating Immune Complexes by the Clq-Protein A Binding Assay, Methods in Enzymology, vol. 74:571–587, 1981.

Virella, G. et al., Isolation of Soluble Immune Complexes from Human Serum: Combined Use of Polyethylene Glycol Precipitation, Gel Filtration, and Affinity Chromatography on Protein A-Sepharose, Methods In Enzymology, vol. 74:644–663, 1981.

Mayer, M. M., The Complement System, Chapter 14, Immunology, edited by Burnet, W. H. Freeman and Company, 1976, pp. 143–155.

Theofilopoulos, A. N. et al., The Biology and Detection of Immune Complexes, Advances in Immunology, 28:89–220, 1977.

Zubler, R. H. et al., Immune Complexes in Clinical Investigation, Recent Advances in Clinical Immunology, Thompson R. A.-Editor Churchill Livingstone, New York, pp. 125–147, 1977.

Carpentier, N. A. et al., Clinical Relevance of Circulating Immune Complexes in Human Leukemia, J. Clin. Invest., 60:874–884, 1977.

Poulton, T. A. et al., Immune Complexes in Ovarian Cancer, The Lancet, pp. 72–73, 1978.

Luthra, H. S. et al., Immune Complexes in Sera and Synovial Fluids of Patients with Rheumatoid Arthritis, J. Clin. Invest., 56:458–466, 1975.

Grigor, R. et al., Systemic Lupus Erythematosus, Annals of the Rheumatic Diseases, 37:121–128, 1978.

Levinsky, J. et al., Serum Immune Complexes and Disease Activity In Lupus Nephritis, The Lancet, p. 564, Mar. 12, 1977.

Theofilopoulos, A. N. et al., Detection of Immune Complexes: Techniques and Implications, Hospital Practice, pp. 107–121, May 1980.

Horowitz, B. et al., Development of Hemagglutination Assays, Vox Sang, 33:324–334, 1977.

Yonemasu, K. et al., Clq: Rapid Purification Method for Preparation of Monospecific Antisera and for Biochemical Studies, the Journal of Immunology, 106, 2:304–313, 1971.

Gabriel, A. et al., Detection of Immune Complexes, Journal of Clin. Invest., 59:990–1001, May 1977.

Heusser, C. et al., Effect of Chemical and Enzymatic Radioiodination on In Vitro Human Clq Activities, Journal of Immunology, vol. 110, 3:820–828, Mar. 1973.

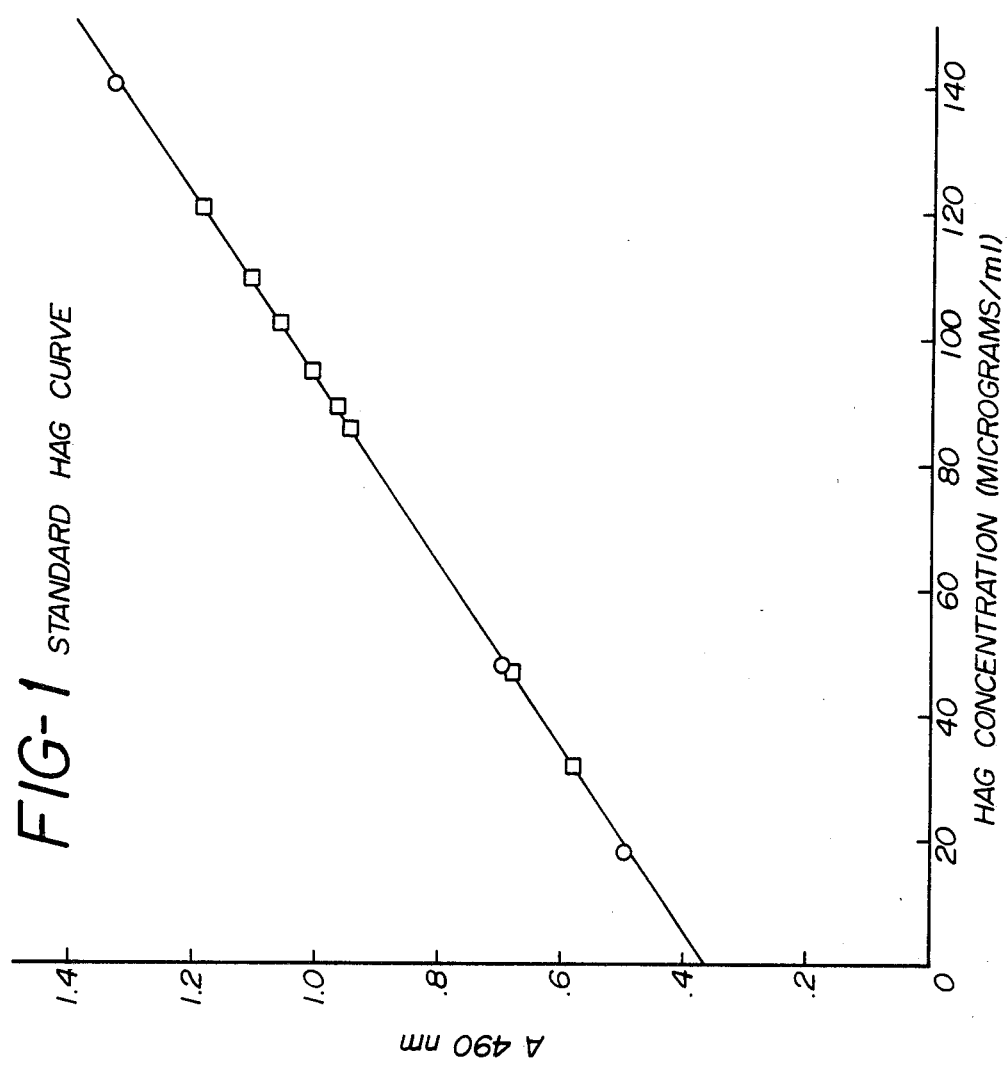
FIG-1 STANDARD HAG CURVE

4,595,654

METHOD FOR DETECTING IMMUNE COMPLEXES IN SERUM

FIELD OF THE INVENTION

This invention relates generally to methods for detecting circulating immune complexes and to reagents useful in these methods and more specifically to a method for detecting human C1q-containing complexes in human serum containing C1, to a test kit for practicing this method, to hybrid cell lines for production of monoclonal antibodies which selectively react with C1q in the presence of C1, and to the monoclonal antibodies so produced.

BACKGROUND OF THE INVENTION

Immune complexes are formed in the blood stream between antigen and antibody as part of the normal immune defense mechanism against pathogens and other foreign substances. These immune complexes allow elimination or neutralization of the foreign antigens and protection of the host. Under some circumstances, however, these immune complexes may themselves cause injury to the host. These circulating immune complexes are relevant to a large number of diseases, especially autoimmune diseases such as rheumatoid arthritis, systemic lupus erythemathosis (SLE), and the like; cancers such as leukemia and ovarian cancer; and a large number of infectious diseases. Particularly in autoimmune diseases, it is useful to detect circulating immune complexes in diagnosing the disease and in monitoring its treatment. See, for example, A. N. Theofilopoulos and F. J. Dixon, Advances in Immunology, Volume 28, Pages 89-220 (1979) and S. E. Ritzmann and J. C. Daniels, Clinical Chemistry, Volume 28, Pages 1259-1271 (1982).

Because of this interest in detecting and monitoring the levels of circulating immune complexes, numerous tests have been described for detecting these complexes. These prior art tests have generally been based on: (a) the detection of epitopes contained in these complexes, (b) the reactivity of these complexes with radiolabeled reagents capable of binding to them, or (c) the binding of the immune complexes to specific receptors found on tissues or cells. An extensive body of art exists describing these tests.

These prior art tests have, however, required the isolation of the putative immune complexes to be detected from human serum because of the presence in the serum of other substances which would cross-react in the test and thus interfere with the detection of the immune complexes. This isolation of the immune complexes from serum has generally been accomplished in the prior art by precipitation (e.g., with polyethylene glycol), by gel filtration chromotography, or by solid phase columns.

The necessity in the prior art tests of isolating the circulating immune complexes from serum prior to performing the test is a difficult, expensive, and time-consuming step. A method which would eliminate the need for immune complex isolation from serum by allowing detection of immune complexes in serum would be of significant advantage. Such an assay would result in significant time saving in performing immune complex assays, would eliminate errors in prior art testing introduced during the isolation step (e.g., incomplete isolation or recovery of the immune complexes), and would eliminate errors introduced by the denaturation of the immune complexes during isolation.

Most antibodies present in immune complexes have a site on the Fc portion of the molecule which reacts with a component of complement. The complement system is part of a complex series of reaction by means of which materials having antibodies bound to them are destroyed by the host's immune system. These complement components are identified by letter and number abbreviations beginning with a capital C. One of particular interest is the first complement component (C1), which itself is made up of subunits designated C1q, C1r, and C1s. It is the C1q subunit of C1 which reacts with the Fc site referred to above.

One of the prior art methods for detecting immune complexes has depended upon the detection of bound C1q (that is, C1q which is attached to the Fc site of antibody in the immune complex). The difficulty with accomplishing such a test in the presence of serum, however, is that prior art materials which have reacted with bound C1q have also reacted with C1 (which contains C1q) circulating in serum. Since this serum C1 is greatly in excess compared to the C1q bound to the complex, it has previously been impossible to conduct a C1q detecting assay in serum.

Since the seminal work of Kohler and Milstein in 1975, much effort has been directed to the production of various hybridomas producing so-called monoclonal antibody. These monoclonal antibodies are extremely useful materials because they have a single specificity, as opposed to so-called polyclonal antibodies resulting from the traditional immunization and bleeding of experimental animals.

Work in this area has simultaneously indicated the rewards and complications of attempting to produce monoclonal antibody from hybridomas. While the general technique is well understood conceptually, there are many difficulties met and variations required for each specific case. In fact, there is no assurance prior to attempting to prepare a given hybridoma that the desired hybridoma will be obtained, that it will produce antibody if obtained, or that the antibody so produced will have the desired specificity. The degree of success is influenced principally by the type of antigen employed and the selection technique used for isolating the desired hybridoma.

Recently, M. D. Golan and co-workers have used the technique of Kohler and Milstein to produce a variety of monoclonal antibodies to C1q and have used these antibodies to study conformational changes in C1q. They reported this work in the Journal of Immunology, Volume 129, Pages 445-447 (August 1982). These antibodies were produced by injecting mice with C1q bound to immune complexes as the antigen, fusing spleen cells from these mice with mouse myeloma cells, culturing the resulting hybridomas, and screening them against human C1q attached via rabbit anti-human C1q to a solid phase. These antibodies reacted with a variety of antigens, but all of them reacted with native serum C1. Many of the antibodies also reacted with fluid-phase C1q. However, these antibodies generally reacted poorly with C1q bound to immune complexes.

The authors concluded that "[t]hese findings demonstrate that the binding of C1q to immune complexes exposes new antigenic determinants". They reached this conclusion because loss of reactivity with their antibodies resulted when the C1q bound to the immune complexes. The antibodies disclosed in this reference would not be useful for a test for immune complexes in serum by detection of Clq bound to immune complexes, because the native serum Cl would clearly obscure any result. In fact, this article appears to suggest that the monoclonal antibody technique would generally not be useful for specific detection of immune complexes.

We have now found that a specific test for immune complexes in serum can be devised using monoclonal antibodies directed at unique epitopes characteristic of Clq bound to immune complexes which are not displayed in native serum Cl.

SUMMARY OF THE INVENTION

In one aspect, the present invention comprises a novel hybridoma capable of producing novel mammalian monoclonal antibody which reacts with human Clq but is substantially non-reactive with human Cl, and the monoclonal antibody produced thereby. The subject monoclonal antibody will selectively react with a human Clq-containing complex in the presence of human Cl and may thus be used to detect immune complexes containing Clq in human serum containing human Cl. Mouse-mouse hybridomas producing mouse monoclonal antibody are preferred.

In a further aspect, the present invention comprises a method and test kit for detection or determination of human Clq-containing complex in a fluid. This method allows detection of the complex in human serum containing native serum Cl. The method comprises the steps of:

(a) providing a selective anti-human-Clq monoclonal antibody attached to a solid phase;

(b) contacting a sample of said fluid with said solid phase under conditions to permit an immunological reaction between said human Clq-containing complex and said anti-human-Clq monoclonal antibody;

(c) separating the unreacted fluid sample from the solid phase;

(d) contacting the solid phase with a labelled second antibody capable of binding to Clq-containing complex which may be bound to said solid phase, under conditions to permit an immunological reaction between said second antibody and said bound complex;

(e) separating unreacted second antibody from the solid phase; and (f) detecting or determining the label present on either said unreacted second antibody or said solid phase and relating said detection or determination to the presence or quantity of Clq-containing complex in the fluid sample.

This fluid is conveniently human serum, but the method may also be used for detecting or determining a human Clq-containing complex in other fluids as well.

The test kit of the invention for detecting human Clq-containing complex comprises a solid phase component having selective anti-human-Clq monoclonal antibody attached thereto and a quantity of labelled second antibody capable of binding to said Clq-containing complex when it is bound to the antibody on said solid phase.

The terms "substantially non-reactive with human Cl" and "selectively reacts with human Clq" mean that the ability of the monoclonal antibody to detect a Clq-containing immune complex is not detrimentally affected by the presence of human Cl or other materials in human serum.

BRIEF DESCRIPTION OF THE DRAWINGS

FIG. 1 represents a standard curve used in the practice of the method of the invention.

DETAILED DESCRIPTION OF THE INVENTION

The subject hybridomas were prepared by the following steps:

A. Immunizing mice with human Clq. While Balb/c female mice were used herein, it is contemplated that other mouse strains or, in fact, other animals such as rats or rabbits, could be used. The immunization schedule and the concentration of Clq antigen should be such as to produce useful quantities of suitably primed splenocytes. Initial immunization with 50 $\mu$g of Clq subcutaneously, followed by a hyperimmunization series of five injections has been found to be effective. Although human Clq was conveniently used as the immunogen herein, it is contemplated that other materials containing Clq-specific antigens or epitopes (including isolated antigens) may be employed.

B. Removing the spleen from the immunized animal and making a spleen suspension in an appropriate medium.

C. Fusing the suspended spleen cells with myeloma cells from a suitable cell line by the use of a suitable fusion promoter. Of course, the myeloma cells selected should be compatible with the spleen cells and should preferably be of the same species. The murine cell line Sp2/0-Ag14 (described in Nature, Volume 276, Pages 269-270, 1978) has been found to be effective for use with the mouse spleen cells employed herein, but it is contemplated that other myeloma cell lines could be used. Many myeloma cell lines (of mice and other animals) are known and available, generally from members of the academic community or various deposit banks, such as the American Type Culture Collection, Rockville, Md. and the Salk Institute Cell Distribution Center, La Jolla, Calif.

The myeloma cell line used should preferably be of the so-called "drug resistant" type, so that unfused myeloma cells will not survive in a selective medium, while hybrids will survive. The most common class of such drug-resistant myelomas are 8-azaguanine resistant cell lines, which lack the enzyme hypoxanthine guanine phosphoribosyl transferase and hence cannot survive in a HAT (Hypoxanthine, Aminopterin, and Thymidine) medium. It is also generally preferred that the myeloma cell line used be of the so-called "non-secreting" type which does not itself produce any antibody, although secreting types may be used. The myeloma used herein is such a non-secreting type. A preferred ratio of cells is about five spleen cells per myeloma cell. While the fusion promoter used in preparing the subject hybridomas was polyethylene glycol having an average molecular weight of about 1000 (commercially available as PEG 1000), other polyethylene glycols and other fusion promoters known in the art may advantageously be employed.

D. Diluting and culturing the mixture of unfused spleen cells, unfused myeloma cells, and fused cells in a selective medium which will not support growth of the unfused myeloma cells for a time sufficient to allow death of all unfused cells (about one week). The medium is one (e.g., HAT medium) which will not support the drug-resistant (e.g., 8-azaguanine resistant) unfused myeloma cell line. Hence, these unfused myeloma cells perish. Since the unfused spleen cells are non-malignant, they have only a finite number of generations and (after a certain period of time) fail to reproduce. The fused cells, on the other hand, continue to reproduce because they possess the malignant quality contributed by the myeloma parent and the enzyme necessary to survive in the selected medium contributed by the spleen cell parent.

E. Evaluating the supernatant in each container (well) containing a hybridoma for the presence of antibody to human Clq (as a first step) and then to human Clq complex.

F. Selecting hybridomas producing the desired antibody. This selection may be, for example, by limiting dilution, in which the volume of diluent is statistically calculated to isolate a certain number of cells (e.g., 1–4) in each separate container (e.g., each well of a microtiter plate). In this way individual hybridomas may be isolated for further cloning.

Once the desired hybridoma has been selected (and cloned if desired) the resulting antibody may be produced in one of two ways.

The purest monoclonal antibody is produced by in vitro culturing of the desired hybridoma in a suitable medium for a suitable period of time, followed by recovery of the antibody from the supernatant. The suitable medium and suitable length of culturing time are known or are readily determined. This in vitro technique produces essentially monospecific monoclonal antibody, essentially free from other specific antihuman immune globulin. There is a small amount of other immune globulin present since the medium contains xenogeneic serum (e.g., fetal calf serum). However, this in vitro method may not produce a sufficient quantity or concentration of antibody for some purposes, since the concentration of monoclonal antibody produced by this method is only about 50 micrograms/ml.

To produce a much greater concentration and quantity of monoclonal antibody, the desired hybridoma may be injected into host animals of the same species as those used to prepare the hybridoma, preferably syngenic or semisyngenic animals. Mice were used in the present invention. This injection is preferably into the peritoneum of the host. The hybridoma will cause formation of antibody-producing tumors in the host after a suitable incubation time, resulting in a very high concentration of the desired antibody (about 5–20 mg/ml) in the blood stream and peritoneal exudate (ascites) of the host. Although these hosts also have normal antibodies in their blood and ascites, the concentration of these normal antibodies is only about five percent of the concentration of the desired monoclonal antibody. Moreover, since these normal antibodies are not antihuman in their specificity, the monoclonal antibody obtained from the harvested ascites or from the serum is essentially free from any contaminating antihuman immune globulin. This monoclonal antibody is normally of high titer (active at dilutions of 1:100,000 or higher) and high ratio of specific to non-specific immune globulin (about 1/20 or greater).

In the practice of the subject method, specific anti-Clq IgG is isolated from the ascites fluid produced as described above by passing the fluid over a chromatography column having protein A attached thereto. Protein A (which may be obtained commercially from Pharmacia Incorporated, Piscataway, New Jersey) is a protein found on the surface of certain species of staphylococcus which attaches to the Fc portion of an IgG molecule and thus allows separation of IgG from contaminating materials.

The IgG fraction is adsorbed onto a solid surface such as the surface of a polystyrene microtiter plate to form the solid phase needed in the subject method. Techniques for coating antibody onto solid surfaces are well-known in the art.

To the wells of this antibody-coated microtiter plate are added samples of the serum to be tested, preferably diluted in buffer. The wells are preferably incubated to allow complete immunological reaction to occur, although such incubation is not essential for operation of the test method. Following the incubation, the fluid in each well is then removed and the wells are washed to remove any remaining unreacted serum.

To detect the presence of Clq complexes coated onto the wells, it is preferred to use an antihuman IgG immune globulin (conveniently rabbit immune globulin) labelled with an enzyme such as horseradish peroxidase. The antihuman IgG is particularly useful for detecting the bound immune complex because it attaches to antigenic sites found on immune complexes but different from those by which the complex is attached to the microtiter plate wells. Methods of attaching enzymes to antibodies are well known in the art. Although an enzyme is the preferred label for detecting the immune complex, other labels such as radioisotopes or fluorochromes may be employed. Moreover, although antihuman immune globulin is the preferred detector, other materials which would bind to the Clq complexes may be used. The detector could, for example, be an antibody to a complement component such as C4b, C3b, or the like or to an antigenic material found in the immune complex such as DNA, hepatitis B antigen, or the like.

After addition of the enzyme labelled rabbit antihuman IgG to the coated wells, the microtiter plates are preferably permitted to incubate to allow complete immunological reaction, although such incubation is not essential. Following the incubation, the unreacted second antibody is removed and the wells are washed to remove any remaining unreacted second antibody. The bound enzyme label may then be detected by addition of the appropriate substrate, which in the case of horseradish peroxidase is o-phenylenediamine. The presence of labelled second antibody and thus of Clq complex is indicated by a color change in the substrate. This test may be simply qualitative (i.e., color or no color) or may be quantitative since the development of color in each well is proportional to the amount of labelled second antibody bound to the solid phase. The relationship between color intensity and Clq complex concentration in serum can be determined from a standard curve prepared by practicing this method upon known materials of varying concentrations. If the label on the second antibody is not an enzyme, the appropriate detecting means (e.g., a scintillation counter for a radioisotope or a fluorescence detector for a fluorochrome) may be employed.

The subject test kit comprises a suitable solid phase surface (such as microtiter wells, beads, or the like) having selective anti-human-Clq antibody attached thereto and a labelled second antibody capable of binding to the Clq-containing complex when it is bound to the antibody on the solid phase. The test kit may also include means for detecting the label on the second antibody (e.g., substrate for the enzyme if an enzyme label is employed), as well as other materials used to practice the subject method.

Although the above method has been described using detection of the bound labelled second antibody as the measure of bound Clq-containing complex, it should also be appreciated that it would be equally possible to determine the amount of unbound labelled second antibody in relation to the amount of second antibody added and to detect the presence of or determine the amount of bound Clq-containing complex from that calculation.

This invention will be further described by the following examples, which are provided to exemplify but not to limit the scope of the subject invention.

EXAMPLE I

Preparation of Clq from Normal Human Serum

A. Buffers (Instructions are included for preparing one liter of each buffer).

1. 0.03M Ethyleneglycol-bis ($\beta$-Aminoethyl Ether) N,N'-Tetraacetic Acid (EGTA Sigma) pH 7.5. Conductivity $2.0 \times 10^{-3}$ Mhos (range $1.95 \times 10^{-3}$ to $2.05 \times 10^{-3}$ Mhos) at 0° C. Dissolve 11.41 g EGTA in 800 ml distilled water. Add 4.5 ml of 50% NaOH to solubilize the EGTA.

When dissolved, cool to +4° C. and make final pH adjustment by dropwise addition of 50% NaOH and then q.s. to 1000 ml with distilled water.

2. 0.069M Ethylenediamine Tetraacetic Acid (EDTA), disodium salt (Sigma) pH 5.0. Conductivity $3.9 \times 10^{-3}$ Mhos (range $3.85 \times 10^{-3}$ to $3.95 \times 10^{-3}$ Mhos) at 0° C.

Dissolve 23.20 g EDTA in 800 ml distilled HOH. When dissolved, cool to +5° C. and adjust pH with 50% NaOH. Q.s. to 1000 ml with distilled water.

3. 0.04M EDTA, disodium salt (Sigma) pH 7.5. Conductivity $3.7 \times 10^{-3}$ Mhos (range $3.65 \times 10^{-3}$ to $3.75 \times 10^{-3}$ Mhos) at 0° C.

Dissolve 13.45 g EDTA in 800 ml distilled water. Cool to +5° C. and adjust pH with 50% NaOH (approximately 2.5 ml). Q.s. to 1000 ml with distilled water.

4. 0.2M Sodium Acetate Buffer pH 5.0 containing 0.75M NaCl and 0.01M EDTA.

Dissolve 2.72 g sodium acetate; 43.83 g NaCl and 3.3 g EDTA in 800 ml distilled water. Adjust pH with 1.0M acetic acid. Q.s. to 1000 ml.

5. 0.005M Sodium Phosphate Buffer pH 7.5, containing 0.75M NaCl and 0.01M EDTA.

Dissolve 1.13 g $Na_2HPO_4$; 0.220 g $NaH_2PO_4 \cdot H_2O$; 43.3 g NaCl; 3.36 g EDTA in 800 ml distilled water. Check pH. Adjust if necessary with 1.0M NaOH or 1.0M HCl. Q.S. to 1000 ml.

6. Stock Sodium Phosphates 0.2M
   a. Dissolve 27.6 g $NaH_2PO_4 \cdot H_2O$ in distilled water and q.s. to 1000 ml.
   b. Dissolve 28.39 g $Na_2HPO_4$ in distilled water and q.s. to 1000 ml.

7. 0.005M Phosphate Buffer pH 7.4 containing 0.65M NaCl and 0.01M EDTA.

Dissolve 37.99 g NaCl and 0.336 g EDTA in approximately 500 ml distilled water. Add 20.75 ml 0.2M $Na_2HPO_4$ (reagent 6.b. above) and 4.25 ml 0.2M $NaH_2PO_4$ (reagent 6.a. above). Adjust pH with 1M NaOH or 1M HCl as required and q.s. to 1000 ml. Deaerate under reduced pressure for at least one-half hour prior to use.

8. 0.005M Phosphate buffer pH 7.4 containing 0.65M NaCl, 0.01M EDTA and 0.2% Sodium Azide.

Dissolve 2 g Sodium Azide in 1000 ml of buffer #7 above.

B. Collection and Preparation of Normal Human Serum.

Whole blood from donors of any ABO type are drawn into tubes without anticoagulant. Blood from individual donors should be kept separate until the beginning of the fractionation. The blood is clotted at room temperature for 60 minutes and then at +5° C. for two hours. Serum is separated at +5° C. by centrifugation at approximately $3000 \times g$. The serum is recentrifuged at $20,000 \times g$ for 60 minutes at +5° C. and free lipid is removed by aspiration. If the serum is not to be used immediately, it should be stored frozen.

C. Fractionation of Serum

1. All steps are done at 5° C. The sera from various donors is pooled and the total volume recorded. The serum is then transferred to Spectrapor #1 dialysis tubing (23 mm flat diameter with M.W. cutoff of 6000 to 8000) and is dialyzed against buffer #1 for 4 hours at +5° C. The buffer is replaced with fresh solution and dialysis is continued for 16 hours as above. The ratio of buffer to serum for these two steps is as follows: Step one—800 ml buffer per 100 ml serum. Step two—2400 ml buffer per 100 ml serum. After dialysis, the insoluble material (Precipitate #1) is removed by centrifugation at approximately $300 \times g$. The supernate is decanted and discarded. The precipitate is washed once with fresh dialysis buffer (#1) taking care to resuspend the precipitate. Wasning is done in approximately the same volume as the starting serum. The precipitate is removed by centrifugation as above. The precipitate is redissolved in buffer #4 at a ratio of 25 ml buffer per 100 ml starting serum by slowly stirring for 15 to 30 minutes. Material is finally centrifuged to remove insoluble aggregates.

2. The redissolved Precipitate #1 above is transferred to dialysis tubing and dialyzed against buffer #2 for 4 hours. For every 100 ml of starting serum, 3200 ml of dialyzing buffer #2 are required. After dialysis, insoluble material (Precipitate #2) is removed by centrifugation at approximately $3000 \times g$. The supernate is decanted and discarded. The precipitate is washed once with fresh dialysis buffer at a volume approximately equal to the volume of Precipitate #1 dialyzed. The precipitate is redissolved in buffer #5 at a ratio of 25 ml buffer per 100 ml of starting serum by stirring gently for 15 to 30 minutes. Material is then centrifuged to remove insoluble aggregates.

3. The redissolved Precipitate #2 is transferred to dialysis tubing and dialyzed against buffer #3 for 5 hours. For every 100 ml of starting serum, 3200 ml of buffer #3 are required. After dialysis, the insoluble material (precipitate #3) is removed by centrifugation at approximately $3000 \times g$. The supernate is decanted and discarded. The precipitate is washed once with fresh dialysis buffer at a volume approximately equal to the volume of Precipitate #2 dialyzed. The precipitate is then redissolved in buffer #7 at a ratio of 1.0 ml buffer per 100 ml of starting serum by stirring gently for 15 to 30 minutes. If more than one centrifuge cup is used to spin down the precipitate, then redissolving buffer should be evenly divided between these cups and only pooled after the precipitate has redissolved. The pooled material is finally centrifuged at $20,000 \times g$ for 15 minutes to remove insoluble aggregates.

D. Preparation and Running of Bio-Gel A5M Column

1. Attach a flow adapter to one end of $2.6 \times 100$ cm column. Block off the effluent tubing. Attach a reservoir to the other end of the column and add approximately 20 ml of deaerated buffer #7.

2. Deaerate 600 ml of Bio-Gel A5M, 200–400mesh media for at least one-half hour and smoothly pour the stirred slurry into the column.

When 2–5 cm bed has formed, allow column to flow. Do not allow to dry.

3. When column is packed, remove excess gel to the desired bed height (100 cm), remove reservoir and attach a flow adapter to the open end.

5. Pack column overnight at 20 ml/hr at 5° C. using a pump.

6. Change flow rate to 5.5 ml/hr and attach to a UV detector set at 280 nm and to a recorder and a fraction collector.

7. Adjust baseline to zero. Set fraction collector for collecting 2.0 ml samples.

8. Pump Clq solution into column and follow with 700 ml deaerated buffer #7.

9. The column is finally treated with 200 ml deaerated buffer containing Sodium Azide (Buffer #8).

10. The Clq peak, which is always the largest on the chromatogram, usually begins to emerge at about the 300 ml mark (tube #150).

The peak samples are pooled according to the following protocol: Draw a tangent from about the midpoint on both the ascending and descending sides of the optical density curve to the baseline. Measure the distance between the two baseline intercepts. Decrease the length of this line by ten percent on either side. Pool the tubes that fall above this line. An example of this procedure appears in FIG. 1.

E. Preparation and Running of Protein A Sepharose CL 4B Column.

1. To a Bio Rad 0.7×10 cm column, add 0.7 g Protein A Sepharose CL 4B. Add 5.0 ml buffer #7 and allow to hydrate and swell for 5–10 minutes.

2. Wash column with approximately 25 ml of buffer #7 by gravity flow.

3. Clamp bottom of column and remove buffer from top of column bed.

4. Fill pump tubing with Clq preparation and attach pump to top of Protein A Column. Pump Clq preparation through column at 20 ml/hr. Collect in single tube. After all of the Clq solution has passed through the column, allow air to be pumped through column to insure complete transfer of the liquid in the column.

5. Regenerate the column with 25 ml. of 0.1M citrate buffer pH 4.5 using gravity flow.

Preparation of Citrate Buffer:
a. 0.1M citric acid ($H_3C_6H_5O_7 \cdot H_2O$).
Dissolve 2.1 g in distilled water and q.s. to 100 ml.
b. 0.1M Sodium Citrate ($Na_3C_6H_5O_7 \cdot 2\,H_2O$).
Dissolve 2.94 g in distilled water and q.s. to 100 ml. Mix 54.5 ml of a. with 45.5 ml. of b. pH=4.5 ±0.1.

6. Equilibrate column with 25 ml Phosphate buffer #8 and store column in same buffer.

F. Determination of Clq Concentration

1. The Clq concentration is determined as follows: An OD 280 nm reading is made using buffer #7 as a blank. Using the extinction value for Clq of $E^{1\,cm} = 6.8$ mg Clq/ml = OD280 × 10/ 6.8.

2. Concentrate the Clq peak to approximately 1.0 mg Clq/ml on an Amicon XM 50 membrane.

This formula is used:
Clq volume after concentration = Clq conc. mg/ml × Volume of Clq before concentration NOTE: Before removing concentrate from chamber, release gas pressure and continue stirring for at least 30 minutes to regain Clq adsorbed to the filter disc.

3. The final concentration of Clq is determined by OD280 nm using the formula from F.1.

G. Purity of Final Product

The purity is determined by polyacrylamide gel electrophoresis in presence of SDS. The procedure is as follows:

1. Reagents
a. Following reagents are supplied by BIO-RAD
DTT (dithiothreitol)
SDS (Sodium dodecyl sulfate)
Ammonium persulfate
Pyronin Y
TEMED (N,N,N'N'Tetramethylethylenediamine)
b. Coomassie Brilliant Blue G-250 (Eastman Kodak)
c. Tank buffer 0.04M Tris; 0.02M Sodium Acetate; 0.002M EDTA pH 7.4 containing 0.1% SDS.
4.85 g Tris (Hydroxymethyl) Aminomethane
2.72 g Sodium Acetate . ($NaC_2H_3O_2 \cdot H_2O$ ).
0.67 g EDTA
1.0 g SDS Dissolve in approximately 800 ml distilled water. Adjust pH to 7.4 with 10% Glacial Acetic Acid. Q.s. to 1 liter with distilled water.

d. Dialysis Buffer: 0.01M Tris HCl, 0.001M EDTA pH 8.0 containing 0.5% SDS.
1.211 g Tris
0.336 g EDTA
1.0 g SDS Dissolve in approximately 800 ml distilled water. Adjust pH to 8.0 with 0.1N HCl. Q.s. to 1 liter with distilled water.

e. Acrylamide-Bis Reagent
Dissolve 5.5 g acrylamide and 0.15 g Bis-acrylamide in distilled water and q.s. to 25 ml.

f. Ammonium persufate 0.1 g/10 ml. distilled water. (Prepare fresh daily).

g. Sample Incubation Solution
0.303 g Tris
0.084 g EDTA

Dissolve in approximately 10 ml distilled water. Adjust pH to 8.0 with 0.1N HCl. In this solution, dissolve the following:
2.5 g SDS
1.54 g DTT
Q.s. 25 ml with distilled water.

h. 0.01% Pyronine Y. Dissolve 0.01 g Pyronin Y in 100 ml distilled water.

i. 30% Sucrose. Dissolve 3 g sucrose in distilled water and q.s. to 10 ml.

j. 25% Isopropyl Alcohol 10% Acetic Acid 0.025% Coomassie Blue G-250.

To approximately 500 ml distilled water, add 250 ml of isopropyl alcohol and 100 ml glacial acetic acid. Dissolve 0.25 g Coomassie Blue G-250 and q.s. to 1 L with distilled water.

k. 10% Isopropyl Alcohol, 10% Acetic Acid, 0.0025% Coomassie Blue G-250.

To approximately 500 ml distilled water add 100 ml isopropyl alcohol and 100 ml glacial acetic acid. Dissolve 0.025 g Coomassie blue G-250 and q.s. to 1 liter with distilled water.

l. 10% Acetic Acid, 0.00125% Coomassie Blue G-250. To approximately 500 ml distilled water add 100 ml glacial acetic acid. Dissolve 0.0125 g Coomassie blue G-250 and q.s. to 1 liter with distilled water.

m. 10% Acetic Acid

To approximately 500 ml distilled water add 100 ml glacial acetic acid. Q.s. to 1 liter with distilled water.

2. Procedure a. Preparation of 10% Acrylamide Gels

Mix together:
- 7.5 ml tank buffer (1.c.)
- 6.75 ml acrylamide-bis solution (1.e.)
- 0.0225 ml TEMED Deaerate for approximately 15 minutes and add 0.7 ml of the ammonium persulfate solution (1.f.).

b. Cover one end of 5×75 mm glass tubes with parafilm and set in Ames Gel Preparation Rack. Add 0.4 ml of 30% sucrose (1.i.) to the bottom of the tubes, taking care not to touch the sides of the tubes. Place plastic tubing 2.5 cm long over open end of tubes and overlay sucrose and fill tubes with the acrylamide solution (2.a.). Allow to polymerize at least 60 minutes. Rinse out sucrose with a couple of washes of tank buffer. Gels can be used immediately or stored for up to 48 hours. If gels are to be stored, fill the washed area with tank buffer and place gels in a humid covered chamber at +5° C.

c. Sample Preparation

One-half ml of the Clq preparation is dialyzed against approximately 500 ml of dialysis buffer (1.d.) overnight at room temperature.

To the dialyzed material add 0.0525 ml of the sample incubation solution (1.g.) plus 0.055 g of sucrose. The solution is incubated at 100° C. in a boiling water bath for three minutes. The sample is tested in triplicate as follows: To 25 μl of the treated sample, add 10 ml of Pyronin Y solution (1.h.) and place on gel. Carefully overlay sample and fill tube with tank buffer. A previously tested Clq sample should be run as a control.

d. Electrophoresis

Samples are electrophoresed in a Canalco Disc electrophoresis cell or equivalent. The lower chamber is filled with approximately 400 ml of tank buffer. The samples are placed in the upper chamber which is then filled with tank buffer. Samples are then electrophoresed at 1 ma/gel for 15 minutes and then at 3 ma/gel until the dye band reaches the bottom of the tubes.

Staining

Gels are stained in a BIO RAD gel electrophoresis diffusion destainer. Alternatively, gels can be stained separately in tubes using at least 50 ml of staining solution per gel. Solutions are kept agitated by placing tubes on a rocking device.

The first staining solution (1.j.) is poured into the destainer (holds approximately four liters). The charcoal cartridge is removed and the destainer is placed on a magnetic stirrer. Samples are stained overnight. The second staining solution (1.k.) is exchanged for the first and staining is carried on as above for 6–9 hours. The third staining solution (1.1.) is exchanged for the second and staining is carried on overnight. The destaining solution (1.m.), is exchanged for the third staining solution, the charcoal cartridge is returned and gels are destained until the background is clear.

f. Interpretation of Gels

The procedure breaks Clq up into three components of 22,000, 27,000, and 29,000 MW. These three components represent the fastest migrating bands on the gel. All other bands are contaminants.

The gels are read on a Photovolt densitometer with an integrating function. The sum of the Clq bands divided by the sum of all bands present is equal to the percent purity of the Clq preparation. The average value of the three gels is taken as the final result.

EXAMPLE II

Production of Monoclonal Antibodies

A. Immunization and Cell Hybridization

Female Balb/c mice (Jackson Laboratories; 6–8 weeks old) were immunized subcutaneously with 50 micrograms of Clq antigen prepared as in Example I. Based on the retroorbital bleed data, one of these mice was selected for the hyperimmunization series of injections, consisting of one initial intraperitoneal injection of one microgram of Clq antigen, followed by four daily successive IP injections of 200 micrograms of Clq antigen plus 80 micrograms of Clq antigen injected IV on days two and three of this four-day period. Following the final immunization, the mouse was sacrificed, the spleen was removed from the mouse, and a single cell suspension was made by pressing the spleen tissue through a stainless steel mesh.

Cell fusion was carried out according to the procedure developed by Kohler and Milstein. Approximately $1.3 \times 10^8$ splenocytes in 10 ml of Dulbecco's modified Eagle medium fortified with l-glutamine and glucose (DME, Gibco, Grand Island, N.Y.) were mixed with approximately $2.6 \times 10^7$ SP2/0-Ag14 myeloma cells in 4.7 ml of DME. The combined cells were centrifuged and the supernatant removed, after which 1 ml of 35% PEG 1000 and 5% DMSO in RPMI 1640 medium (Gibco) was added with mixing. This addition was followed by addition of two successive quantities of DME (1 ml and 2 ml) with mixing, followed by addition of a 4 ml and then an 8 ml quantity of HT medium (this HT medium comprised 68 mg hypoxanthine and 36.5 mg thymidine in 500 ml DME). After these successive addition and mixing steps, the whole was centrifuged, the supernatant was removed, and the resulting pellet of cells was resuspended in 40 ml of HT medium and incubated overnight.

B. Selection and Growth of Hybridomas

After cell fusion, cells were cultured at HT medium at 37° C. with 6% $CO_2$ in a 100% humidity atmosphere. The following day, the suspended cells were diluted to 400 ml with HAT medium and one ml of this solution was placed in each well of a series of microtiter plates. The plates were further incubated at 37° C. and 6% $CO_2$ and 100% humidity for about two weeks.

Supernatants above cultures containing hybridomas were subjected to a preliminary screen to determine their reactivity to the human Clq antigen used initially to immunize mice in the production of hybridomas. An ELISA assay was conducted by coating human Clq onto the surface of wells of microtiter plates, followed by addition of the supernatant samples. After removal of the unreacted supernatant, the presence of anti-Clq antibody was detected using rabbit antimouse IgG labelled with horse radish peroxidase enzyme (Miles-Yeda). Hybridomas producing antibodies that reacted with human Clq were subcultured and cloned for further screening.

The particular hybridomas which were to be further screened were injected into mice to produce ascites fluid and the resulting ascites fluid was purified by flowing over a protein A column to isolate the IgG fraction. This IgG fraction was diluted in a carbonate buffer (1.59 g $Na_2CO_3$, 2.93 g $NaHCO_3$, and 0.2 g $NaN_3$ q.s. one liter with water) to a concentration of 50 mg/ml. A 0.2 ml aliquot was added to each well of a Dynatech substrate plate, after which the plate was covered tightly with parafilm and incubated at 2°–8° C. for 16–22 hours. Following this incubation, the fluid in each well was removed and the wells were washed three times with BPS-Tween (8.0 g NaCl, 0.2 g KH$_2$PO$_4$, 2.9 g Na$_2$HPO$_4$·12 H$_2$O, 0.2 g KCl, and 0.5 ml Tween 20 diluted in water to make one liter of solution).

The antibodies were evaluated by using a human serum known to contain immune complexes. This serum was diluted 1:5 by the addition of four volumes of PBS Tween to one volume of serum. A 0.2 ml aliquot of the diluted serum was added to each well containing test antibody, and the trays were then tightly covered with parafilm and incubated 60 minutes at 37° C.( Following the incubation, the fluid in each well was removed and the wells were washed three times with PBS-Tween. The rabbit anti-mouse IgG/horse radish peroxidase conjugate (Miles-Yeda) was diluted 1:10,000 with PBS-Tween and a 0.2 ml aliquot of this diluted conjugate was added to each coated well. Following a further 60 minute incubation at 15°–25° C. in the dark, the fluid in each well was removed and each well was washed three times with PBS-Tween. Finally, the presence and quantity of enzyme labelled antibody in each well was detected by adding peroxide substrate and determining the intensity of color produced.

Of the approximately 35 hybridomas which were positive in the initial screening, five were acceptably positive and selective against Clq-containing complex. Two of these (designated 4A4B11 and 12A5B7) were the best and were selected to be used in the preparation of test kits.

EXAMPLE III

Test Kit Preparation

The ascites fluid from hybridomas 12A5B7 and 4A4Bll were purified on protein A columns as previously described. The protein fraction obtained was diluted in the previously-described carbonate buffer to a concentration of 50 micrograms/ml and a 0.2 ml aliquot was added to each well of a Dynatech substrate plate. Following this addition, the plate was covered tightly with parafilm and incubated at 2°–8° C. for 16–22 hours. Following the incubation, the fluid in each well was removed and the tray wells were washed three times with the previously-described PBS-Tween. These tray wells coated with specific anti-Clq monoclonal antibody form the solid phase to be used in the subject test kit.

The other ingredients of the test kit are the anti-human IgG/enzyme conjugate, the PBS-Tween solution, the substrate for the enzyme, and the controls. These other materials would generally be included in a kit for convenience and standardization. The control substances used in the subject test kit are human serum to which differing amounts of lyophilized heat-aggregated IgG has been added.

Kit Components

Typical kit components in the preferred embodiment of the invention are the following:

- 6 Microtitration Plates (96 wells per plate) coated with Monoclonal Antibody (Murine) to Human Clq; contains 0.02% Thimerosal 6 packets Phosphate-Buffered Saline (PBS) in crystalline form; each packet contains 8 g NaCl, 0.2 g KH$_2$PO$_4$, 1.16 g Na$_2$HPO$_4$, 0.2 g KCl, and 0.2 g thimerosal 1 vial Polysorbate 20—polyoxyethylene sorbitan monolaurate, Sigma 1 vial Conjugate Concentrate—monoclonal anti-human IgG (Murine) conjugated to horseradish peroxidase; contains 0.02% Thimerosal and 0.005% Gentamicin Sulfate. The configuration is performed by the method of Nakane, et al. J. Histochem and Cytol., 22, 1084–1974. A typical titer of the ascites against human IgG is $8 \times 10^5$. The resulting material is diluted with fetal calf serum to yield a material having the following properties: A 492 with 150 mg/ml HAG<1.5; $r^2$>0.95; slope>0.5; and y-intercept<0.04. A typical dilution is 1:100 to yield the Conjugate Concentrate.

2 vials o-Phenylenediamine.2 HCl (OPD) tablets; each tablet contains sufficient OPD and buffer so that 100 ml of substrate solution contains 26.5 mg citric acid, 73.0 mg Na$_2$HPO$_4$, and 35.0 mg of OPD.

1 vial 3% Hydrogen Peroxide; contains N-Phenylacetamide 2 vials High Normal Control (Human serum to which lyophilized heat aggregated IgG has been added)

2 vials Low Abnormal Control (Human serum to which lyophilized heat aggregated IgG has been added)

2 vials High Abnormal Control (Human serum to which lyophilized heat aggregated IgG has been added)

EXAMPLE IV

Summary of Test Procedure

A. Specimen Collection

No special preparation of the individual is required prior to specimen collection. The whole-blood test specimen should be collected by accepted medical techniques. The specimen must be allowed to clot for at least two hours at room temperature (20° to 30° C.) before the serum is removed.

B. Preparation of Reagents

1. Preparation of PBS-Polysorbate: Completely dissolve the contents of one packet of PBS in one liter of glass distilled or deionized water. Add 0.5 ml of Polysorbate 20 and mix. PBS-Polysorbate is stable for one month when stored at room temperature.

2. Preparation of Conjugate: Disposable glass or plasticware must be used. The Conjugate Concentrate must be diluted with PBS-Polysorbate prior to use. For a typical dilution ratio of 1:50, add 0.4 ml of Conjugate Concentrate to 19.6 ml PBS-Polysorbate. A volume of 20 ml is needed for one microtitration plate. The Conjugate should be prepared just prior to use and should be used within 30 minutes.

3. Preparation of Substrate: Disposable glass or plasticware must be used.

a. Completely dissolve eight OPD tablets in 24 ml of glass-distilled or deionized water. Allow approximately 10 minutes for the tablets to dissolve. An aliquot mixer can be used for easy dissolution of the tablets.

b. Just prior to use, add 100 ul hydrogen peroxide and mix. This volume is sufficient for one microtitration plate. The Substrate is stable for 30 minutes at room temperature in the dark. The Substrate should be clear to very pale yellow. If it is noticeably yellow in color, discard and prepare more Substrate as required.

4. Preparation of 4N Sulfuric Acid: Add 1 ml of concentrated (36N) sulfuric acid to 8 ml of glass-distilled or deionized water. Always add the acid to the water.

Never reverse the procedure. This volume is sufficient for one microtitration plate.

5. Reconstitution of Lyophilized Controls: Reconstitute one vial of each control (High Normal Control, Low Abnormal Control and High Abnormal Control) by adding 0.5 ml glass-distilled or deionized water to each vial. Add water to the vial and gently resuspend the powder. Allow the rehydrated controls to stand at room temperature (20° to 30° C.) for 15 minutes prior to use. Do not vortex or mix vigorously. Vigorous mixing will cause denaturation of the serum IgG and result in abnormally high values. Reconstituted controls may be used for one working day. Each reconstituted vial of control is sufficient for duplicate wells on each of five microtitration plates if they are run during the same working day.

C. Test Procedure

1. Prepare PBS-Polysorbate. Refer to Preparation of Reagents.

2. Using disposable glass tubes, prepare 1:5 dilutions of the three reconstituted controls and the serum specimens in PBS-Polysorbate. Mix gently by inversion. Do not vortex. Example: 0.125 ml of control or serum specimen plus 0.5 ml of PBS-Polysorbate (sufficient volume for duplicate testing).

3. Remove the protective cover tape from the Microtitration Plate coated with Monoclonal Antibody (Murine) to Human Clq immediately prior to use.

4. Empty wells of the microtitration plate by vigorously shaking out contents.

5. Wash the microtitration plate (including blanking wells) three times with PBS-Polysorbate. After the last wash, tap plates firmly on absorbent paper to remove excess PBS-Polysorbate. Use the microtitration plates immediately after washing. Do not allow control and test wells in the microtitration plate to dry.

6. Place the microtitration plate on top of a Plate Guide. The first vertical row of wells on the left is reserved for blanking the microtitration plate reader. Refer to the manufacturer's instructions for blanking the reader. No additions except PBS-Polysorbate wash solution are to be made to this row of wells until the substrate addition of the test procedure.

7. Label the microtitration plate for high normal, low abnormal, high abnormal and reagent controls, in duplicate, followed by serum specimens.

NOTE: The controls and serum specimens in steps 8–10 should be added to the microtitration plate within 10 minutes. Pipette tips should be changed for each different control and test specimen.

8. Add 200 μl of each diluted control, in duplicate, to the appropriate wells.

9. Add 200 μl PBS-Polysorbate to the duplicate reagent control wells and the blanking wells.

10. Add 200 μl of each diluted serum specimen to the appropriate wells. Serum specimens should be tested in duplicate until precision is attained by the operator so that the coefficient of variation between duplicates is consistently less than 10 percent.

11. Cover the microtitration plate with a plate cover and incubate trays in a moist environment at 32° to 37° C. for 60 minutes.

a. In a 37° C. water bath:
The covered plate should not be floated on the water, but rested on a level support in the water bath. Keep bath covered during incubation. Air temperature at level of plate should be 32° to 37° C.

b. In a 37° C. air incubator:
Place a container with a cover inside the incubator. Leave this container inside the incubator to be sure the temperature inside is 37° C. Maintain moisture by having damp paper towels in the bottom of the container. Place microtitration plate inside the container and keep the cover on for the incubation period.

12. Prepare Conjugate. Refer to Preparation of Reagents.

13. Wash the microtitration plate (including blanking wells) three times with PBS-Polysorbate using the ELISA multichannel wash bottle. The washing procedure must be thorough:

a. Empty wells by vigorously shaking out contents.

b. Invert wash bottle and thoroughly flush the wells with PBS-Polysorbate by squeezing the bottle forcefully.

c. Remove PBS-Polysorbate by vigorously shaking out contents.

d. Repeat steps 13b and 13c twice.

e. After the final wash, tap the inverted plate firmly on a clean paper towel to remove excess PBS-Polysorbate.

f. Proceed immediately to the next step.

Gloves should be worn during washing steps. Household bleach should be added to waste material prior to disposal.

NOTE: Do not allow the wells to dry during the test. Drying of the wells may result in falsely high absorbance values.

14. Using a multichannel micropipette, add 200 μl of Conjugate to all wells, except the blanking wells.

15. Cover the microtitration plate with a plate cover and incubate plates at room temperature in the dark for 60 minutes.

16. Prepare Substrate 10 minutes prior to use. The Substrate should be clear to very pale yellow in color. Refer to Preparation of Reagents.

17. Wash the microtitration plate as described in Step 13. Proceed immediately to the next stop.

18. Using a multichannel micropipette, add 200 μl of Substrate to all wells, including the blanking wells.

19. Place the microtitration plate, uncovered, in the dark at room temperature for 30 minutes.

20. Using a multichannel micropipette, forcibly eject 50 μl of 4N sulfuric acid into each well, including the blanking wells. It is important that the sulfuric acid is spread quickly and uniformly throughout the well to completely inactivate the enzyme. Results can be read up to one hour after the sulfuric acid is added if plates are stored in the dark.

21. Set the microtitration plate reader at wavelength of 488 to 492 nm and blank the reader according to the manufacturer's instructions by using the blanking well(s) containing Substrate and acid.

22. Measure the color intensity in all microtitration wells.

INTERPRETATION OF RESULTS

A. Test Controls

1. Reagent Control: Calculate the mean absorbance value of the duplicate Reagent Control. The mean absorbance value must be less than 0.05. If equal to or greater than 0.05, the test should be repeated using freshly prepared reagents.

2. Normal and Abnormal Controls: Calculate the mean absorbance value of the duplicate high normal, low abnormal and high abnormal controls. Duplicates should be within 20 percent of the mean.

B. Preparation of the Standard Curve and Determination of the Immune Complex Concentration (micrograms/ml HAG equivalents) for each serum 1. Graphic Method a. Plot the mean absorbance values for the normal, low abnormal and high abnormal controls against the corresponding micrograms/ml HAG equivalents on linear graph paper. Typical mg/ml HAG equivalents are 20 for the Low Abnormal Control, 50 for the Normal Control, and 140 for the High Abnormal Control.

b. Draw a straight line for the best fit of the plotted points.

c. On the curve, locate the point corresponding to the absorbance value (or average absorbance value if duplicates were performed) of each serum and read off the corresponding micrograms/ml HAG equivalents.

d. Report immune complex concentration in micrograms/ml HAG equivalents as determined above.

2. Calculation Method

Calculations can be made on a variety of calculators supplied with linear regression programs. Follow the manufacturer's instructions for use of these programs to establish the standard curve and the immune complex concentration (micrograms/ml HAG equivalents) of each test sample.

C. Intepretation of Results

1. Negative Results

Results from 0 to 34 micrograms/ml HAG equivalents can be interpreted as negative for significant levels of circulating immune complexes.

2. Positive Results

Results of >35 micrograms/ml HAG equivalents can be interpreted as positive for significant levels of circulating immune complexes.

EXAMPLE V

Detection of Circulating Immune Complexes in the Serum of Patients with Active Diseases Collection of Serum Supplies Whole blood samples were obtained from the patients and allowed to clot at ambient temperature for at least two hours after which the serum was centrifuged. The clear serum was carefully separated from the cellular elements and kept in glass tubes until testing. Excess serum was aliquoted into 0.5 ml fractions and frozen at −70° C. for use in future testing.

Testing of Serum Samples

Procedure set out in Example IV

Interpretation of Data

A. Absorbance Readings (492 nm): Absorbance readings were obtained on a Dynatech Model MR600 microtitration plate reader.

| Patient | Sex | Diagnosis | A492 |
|---|---|---|---|
| H.R. | F | Rheumatoid Arthritis | 1.064 |
| G.T. | F | Rheumatoid Arthritis | 1.130 |
| Y.O. | F | Rheumatoid Arthritis | 1.015 |
| N.M. | M | Rheumatoid Arthritis | 1.102 |
| D.M. | F | Systemic Lupus Erythematosis | 0.946 |
| B.R. | F | Systemic Lupus Erythematosis | 0.973 |
| S.D. | M | Acute Hepatitis B | 1.186 |
| R.V. | M | Acute Hepatitis B | 1.067 |
| E.L. | M | AIDS Patient | 0.581 |
| T.D. | M | AIDS Patient | 1.138 |
| R.W. | M | Normal | .397 |
| K.C. | F | Normal | .248 |

B. Standard Curve Preparation:

1. A standard curve was prepared using three heat aggregated standards (See FIG. 1).

2. The curve is linear from 25 $\mu$g/ml to 150 $\mu$g/ml

C. Determination of Immune Complex Concentration in Patient Sera:

Using the A492 values for each sera, the immune complex concentration for each sample analyzed was determined to be as follows:

| Patient | A492 | Immune Complex Conc. ($\mu$g/ml HAG eq) |
|---|---|---|
| H.R.(RA) | 1.064 | 102 |
| G.T.(RA) | 1.130 | 109 |
| Y.O.(RA) | 1.015 | 96 |
| N.M.(RA) | 1.102 | 108 |
| D.M.(SLE) | 0.946 | 85 |
| B.P.(SLE) | 0.973 | 89 |
| S.D.(Hep.B) | 1.186 | 120 |
| R.V.(Hep.B) | 1.067 | 108 |
| E.L.(AIDS) | 0.681 | 47 |
| T.D.(AIDS) | 1.138 | 109 |
| R.W.(Normal) | .397 | <10 |
| K.C.(Normal) | .248 | <10 |

D. Patient Evaluation:

Immune Complex Concentrations of >35 $\mu$g/ml HAG are positive for significant levels of circulating immune complexes. All patients having active disease tested positive, while the normals tested negative.

EXAMPLE VI

Use of the Subject Test for Detection of AIDS Risk Group

The C1q complex test kit described in Example III was used to evaluate the AIDS risk groups, both those having AIDS and those not having AIDS. These groups have significant concentrations of circulating immune complexes in their blood. This testing was conducted in comparison to the current staphylococcus binding assay and C1q binding assay used for detection of immune complexes.

The results of this comparative testing are shown in Table I.

TABLE 1

| Group | SBA | Test C1q BA | Subject test |
|---|---|---|---|
| AIDS: | | | |
| homosexual cases | 125(105);19;68% | 13(9);19;43% | 89(47);16;100% |
| heterosexual cases | 100(79);7;86% | 9(5);7;43% | 69(51);6;83% |
| Haitian cases | 159(78);19;100% | 16(7);19;89% | 125(50);13;100% |
| Total AIDS | 136(91);45;84% | 14(8);45;67% | 99(52);35;97% |
| Lymphadenopathy | 105(70);36;92% | 12(7);36;72% | 66(46);28;80% |
| Controls: | | | |
| homosexual | 56(56);51;53% | 10(7);51;55% | 73(42);40;95% |
| Haitians | 21(25);8;13% | 5(1);8;0% | 40(22);7;71% |
| normals | 9(10);23;0% | 6(1);23;9% | 4(10);21;5% |

Results are presented as follows: mean score (standard deviation); number tested; % positive
Upper limits of "normal" values:
SBA 34 mg
C1q BA 8
Subject Test 23

This table indicates that the subject test detected 97% of the AIDS victims, while also detecting substantial proportions of the various AIDS risk groups not currently carrying AIDS, such as homosexuals and Haitians. There were 5% false positive values. By comparison to the prior art tests, the subject test was far superior both in detection of actual AIDS victims and in detection of the AIDS risk groups.

EXAMPLE VII

Monoclonal Antibody Characterization

An SDS polyacrylamide gel electrophoresis analysis was performed on the monoclonal antibodies produced by both hybridomas described herein against a range of low molecular weight standards. By six-point linear regression, the heavy chain of each antibody was determined to be 52,384, while the light chain of each was determined to be 26,128.

An electrofocusing analysis gave the following results: For the 4A4B11 antibody pI's were observed at 6.6, 6.5, 6.4, and 6.35; for the 12A5B7 antibody pI's were observed at 6.1, 6.05, 5.95, and 5.9.

Both antibodies were determined to be $IgG_1$ by conventional techniques.

As described above, the subject monoclonal antibody is useful for detecting the presence of human C1q-containing complexes, especially in human serum containing C1, and thus obviates the necessity of separating the C1q-containing complexes from serum before testing, as has been required by prior art tests. The monoclonal antibody may be used in the subject method and test kit for detection of C1q-containing complexes, particularly in serum, which detection is useful in the diagnosis of disease and in the monitoring of the treatment of such disease.

According to the present invention, hybridomas are provided which are capable of producing antibody that reacts with human C1q but is substantially unreactive with human C1. Also provided are the monoclonal antibody, methods for producing this hybridoma, methods of producing the monoclonal antibody, and methods and test kit for using the antibody to detect human C1q-containing complexes.

Although only two hybridomas producing two monoclonal antibodies specific for C1q have been described, it is contemplated that the present invention encompasses all monoclonal antibodies exhibiting this specificity and all hybridomas capable of producing such monoclonal antibodies. It was determined that the subject antibodies belong to the subclass $IgG_1$, which is one of four subclasses of murine IgG. These subclasses of IgG differ from one another in the so-called "fixed" regions, although an antibody to a specific antigen or epitope will have a so-called "variable" region which is functionally identical regardless of which subclass of IgG to which it belongs. That is, a monoclonal antibody exhibiting the characteristics described herein may be of subclass $IgG_1$, $IgG_2a$, $IgG_2b$, or $IgG_3$, or of classes IgM, IgA, or other known Ig classes. The differences among these classes or subclasses will not effect the selectivity of the subject antibody, but may effect the further reaction of the antibody with other materials, such as (for example) complement or anti-mouse antibodies.

Following the disclosure set out herein, one may readily prepare other hybridomas producing monoclonal antibodies which selectively react with C1q. Such other hybridomas and monoclonal antibodies are considered to be within the scope of the present invention, regardless of whether or not they react with the same epitope on C1q as do the two exemplary antibodies disclosed herein.

Included in the subject invention are methods for preparing the monoclonal antibodies described above employing the hybridoma technique illustrated herein. Although only two examples of hybridomas are given, it is contemplated that one skilled in the art could follow the immunization, fusion, and selection methods provided herein and obtain other hybridomas capable of producing antibodies having the selectivity described. Since the individual hybridomas produced from a known mouse myeloma cell line and spleen cells from a known species of mouse cannot be further identified except by reference to the antibody produced by the hybridoma, it is contemplated that all hybridomas producing antibody having the activity described above are included within the subject invention, as are methods for making the antibody employing the hybridoma.

It is also contemplated that other antibody-producing mammalian species could be used to generate hybridomas having the specificity described herein. One could, for example, immunize rats following the techniques described above and fuse the rat splenocytes with a rat myeloma line. Techniques for performing such rat-rat fusions are well known.

The two hybridomas exemplified above were deposited with the American Type Culture Collection, 12301 Parklawn Drive, Rockville, Md. 20852, on July 29, 1983, and were assigned the ATCC accession numbers HB8327 (for hybridoma 4A4B11) and HB8328 (for hybridoma 12A5B7).

What is claimed is:

1. An IgG mouse antibody, produced by a mouse lymphocyte:myeloma hybridoma cell, which specifically binds to human C1q and human C1q containing complexes but which substantially does not bind to human C1.

2. Mouse monoclonal antibody which specifically binds to human C1q and C1q-containing complex in human serum containing human C1, but which does not detectably bind to human C1, said antibody of the IgG class and produced by a mouse lymphocyte:myeloma hybridoma cell.

3. The monoclonal antibody of claim 2 which is produced by hybridoma ATCC HB8327 or HB8328.

4. A hybridoma capable of producing a mouse monoclonal antibody of the IgG class which specifically binds to human C1q and human C1q-containing complexes, but which does not detectably bind to human C1.

5. A mouse-mouse hybridoma capable of producing a monoclonal antibody of the IgG class which selectively binds to human C1q and human C1q-containing complex in human serum containing human C1, but which does not detectably bind to human C1.

6. The hybridoma of claim 5 formed by fusion of cells from a mouse myeloma line and spleen cells from a mouse proveiously immunized with human C1q.

7. The hybridoma of claim 6 which is ATCC HB8327 or HB8328.

8. A metod for detection or determination of a human C1q-containing complex in a fluid suspected to contain said complex which comprises:
    (a) providing a mouse monoclonal antibody of the IgG class and produced by a mouse lymphocyte:-myeloma hybridoma cell and capable of specifically binding to human C1q and human C1q-containing complexes, but not detectably bind to human C1q, said antibody being attached to a solid phase;

(b) contacting a sample of said fluid with said solid phase under conditions to permit an immunological reaction between said human Clq-containing complex and said anti-human-Clq monoclonal antibody;

(c) separating the unreacted fluid sample from the solid phase;

(d) contacting said solid phase with a labelled second antibody capable of binding to Clq complex which may be bound to the solid phase under conditions to permit an immunological reaction between said second antibody and said bound complesx;

(e) separating unreacted second antibody from the solid phase; and (f) detecting or determining said label on either said solid phase or said unreacted second antibody and relating said detection or determination to the presence or quantity of Clq-containing complex in said fluid sample.

9. The method of claim 8 wherein said fluid is human serum containing native Cl.

10. The method of claim 8 wherein said second antibody is non-human anti-human IgG.

11. The method of claim 8 wherein said label is a radioisotope, an enzyme, or a fluorochrome.

12. The method of claim 8 wherein the selective anti-human-Clq monoclonal antibody is selected from those produced by hybridomas ATCC HB8327 and HB8328.

13. A test kit for detection of human Clq-containing complex which comprises:

(a) a solid phase having attached thereto mouse monoclonal antibody of the IgG class and produced by a mouse lymphocyte-myeloma hybridoma cell, said antibody capable of specifically binding to human Clq and human Clq-containing complexes, but not detectably bind to human Cl; and (b) a container having a labelled second antibody capable of binding to said Clq-containing complex when said complex is bound to the antibody on said solid phase.

14. The kit of claim 13 wherein said solid phase is the well of a microtiter plate.

15. The kit of claim 13 wherein the selective anti-human Clq monoclonal is selected from the antibodies produced by hybridomas ATCC HB8327 and HB8328.

16. The test kit of claim 13 wherein said labelled second antibody is non-human anti-human IgG.

17. The test kit of claim 13 wherein the label on said labelled second antibody is selected from the group consisting of radioisotopes, enzymes, and fluorochromes.

18. The test kit of claim 13 which further comprises means for detecting the label on said second antibody.

19. The test kit of claim 13 in which the label on said second antibody is an enzyme and which further includes a substrate for said enzyme, which substrate changes color when acted upon by the enzyme.

* * * * *